United States Patent [19]

Kristiansen et al.

[11] Patent Number: 5,302,605

[45] Date of Patent: Apr. 12, 1994

[54] PICOLINE OXIDES

[75] Inventors: Odd Kristiansen, Möhlin; Laurenz Gsell, Basel; Peter Maienfisch, Rodersdorf, all of Switzerland

[73] Assignee: Ciba-Geigy Corporation, Ardsley, N.Y.

[21] Appl. No.: 758,932

[22] Filed: Sep. 11, 1991

[30] Foreign Application Priority Data

Sep. 18, 1990 [CH] Switzerland .................. 3016/90

[51] Int. Cl.$^5$ .................. A61K 31/44; C07D 401/06
[52] U.S. Cl. .................. 514/341; 514/275; 514/256; 544/331; 544/333; 546/278
[58] Field of Search ............... 546/278; 544/331, 333; 514/341, 275, 256

[56] References Cited

U.S. PATENT DOCUMENTS

| | | | |
|---|---|---|---|
| 3,708,580 | 1/1973 | Miller et al. | 514/80 |
| 4,678,795 | 7/1987 | Shiokawa et al. | 514/341 |
| 4,742,060 | 5/1988 | Shiokawa et al. | 514/252 |
| 4,803,277 | 2/1989 | Shiokawa | 514/332 |
| 4,876,263 | 10/1989 | Shiokawa | 514/324 |
| 4,902,689 | 2/1990 | Gesing | 544/280 |
| 4,913,113 | 4/1990 | Shiokawa | 514/333 |
| 4,918,086 | 4/1990 | Gsell | 514/351 |
| 4,968,695 | 11/1990 | Wolf | 514/63 |
| 5,032,589 | 7/1991 | Shiokawa | 514/245 |

OTHER PUBLICATIONS

Bickel Pharmacological Reviews vol. 21, No. 4. p. 325. 339–341, 352, 1969.

*Primary Examiner*—Jane T. Fan
*Attorney, Agent, or Firm*—Marla J. Mathias; Kevin T. Mansfield

[57] ABSTRACT

Novel 3-picoline-N-oxides of formula I

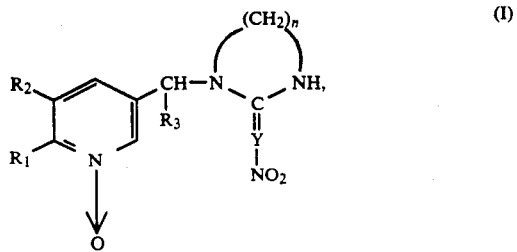

wherein $R_1$ and $R_2$ independently of each other are hydrogen or halogen, $R_3$ is hydrogen or $C_1$–$C_4$alkyl, n is the number two or three, and Y is nitrogen or the methine group, can be used as pesticides. Especially insects are controlled.

3 Claims, No Drawings

PICOLINE OXIDES

The present invention relates to novel derivatives of 3-picoline-N-oxide, to processes for the preparation thereof, to pesticides that comprises those compounds, and to the use thereof in the control of pests, especially insects.

The 3-picoline-N-oxide derivatives according to the invention correspond to formula I

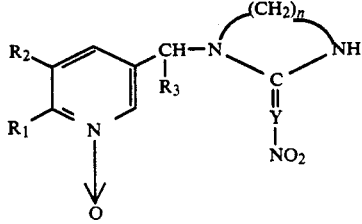

wherein $R_1$ and $R_2$ independently of each other are hydrogen or halogen, $R_3$ is hydrogen or $C_1$–$C_4$alkyl, n is the number two or three, and Y is nitrogen or the methine group.

In the literature, heterocyclic compounds that contain a nitroguanidine structure or nitroethylene structures are known as insecticides from EP-A-192 060. However, the biological properties of these compounds are not completely satisfactory in pest control.

The compounds of formula I can occur in the form of the tautomers of formula Ia

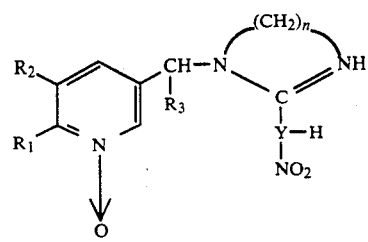

Formula I according to the invention is herein to be understood as including formula Ia.

Furthermore, formula I according to the invention also covers the possible E- and Z-isomers of formulae Ib and Ic

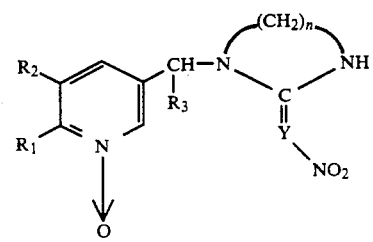

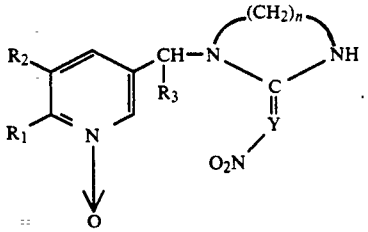

In the definition of formula I according to the invention, the individual generic terms are to be understood as having the following meanings:

The halogen atoms that come into consideration as substituents are fluorine and chlorine as well as bromine and iodine, with fluoride, chlorine and bromine, but especially chlorine, being preferred.

The alkyl radicals that come into consideration as substituents can be straight-chained or branched. Examples of such alkyl radicals that may be mentioned are methyl, ethyl, propyl, isopropyl, butyl, isobutyl, sec-butyl and tert-butyl.

Of the compounds of formula I, prominence is to be given to those sub-groups wherein either a) $R_1$ and $R_2$ independently of each other are hydrogen or chlorine, or b) $R_3$ is hydrogen.

Of sub-group a), preference is given to those compounds wherein $R_1$ is chlorine and $R_2$ is hydrogen.

An especially preferred group of compounds of formula I consists of those compounds wherein $R_1$ is chlorine and $R_2$ and $R_3$ are hydrogen.

There may be mentioned as preferred individual compounds of formula I:

3-(2-nitromethylidene-imidazolidin-1-ylmethyl)-pyridine-N-oxide, 2-chloro-5-(2-nitromethylidene-imidazolidin-1-ylmethyl)-pyridine-N-oxide and 2-chloro-5-(2-nitroimino-imidazolidin-1-ylmethyl)-pyridine-N-oxide.

The compounds of formula I according to the invention can be prepared analogously to known processes. For example, the compound of formula I is obtained by reacting a halo-3-picoline-N-oxide of formula II

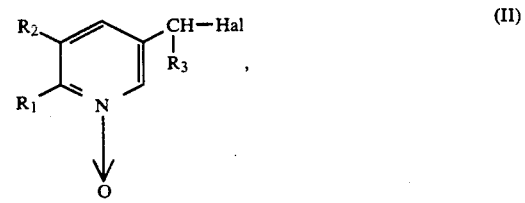

wherein $R_1$, $R_2$ and $R_3$ are as defined under formula I and Hal is halogen, preferably chlorine or bromine, in the presence of an acid-binding agent with a cyclic amine of formula III

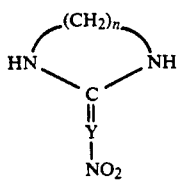
(III)

wherein n and Y are as defined under formula I.

The process according to the invention (II+III→I) is advantageously carried out in an inert solvent at temperatures of from −10° C. to +100° C., especially from 0° C. to +80° C.

There are suitable as solvents especially polar aprotic solvents, such as dimethylacetamide, 1-methylpyrrolidone, dimethyl sulfoxide, sulfolane, tetrahydrofuran, dioxane, acetonitrile or dimethylformamide. There are suitable as acid-binding agents carbonates, such as sodium carbonate or potassium carbonate, hydroxides, such as sodium hydroxide or potassium hydroxide, or hydrogen carbonates, such as sodium hydrogen carbonate or potassium hydrogen carbonate. Tertiary organic amines, such as triethylamine or diethylaniline, are also suitable acid-binding agents. Hydrides, such as sodium hydride, can also be used as acid-binding agents. For example, when sodium hydride in acetonitrile or dimethylformamide is used, the reaction temperature can be lowered to from 0° C. to +25° C. without the reaction time being substantially increased as a result. Advantageously, the reaction can also be facilitated by the addition of a catalytically active salt, such as caesium chloride.

The intermediates of formulae II and III are known or can be prepared analogously to known processes.

For example, the halo-3-picoline-N-oxides of formula II are obtained by reacting halo-3-picoline of formula IV

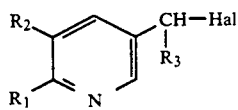
(IV)

with an oxidising agent, such as an organic per-acid, for example 3-chloroperbenzoic acid, or hydrogen peroxide, or with a per-acid produced in situ, such as in the systems $H_2O_2$/glacial acetic acid or $H_2O_2$/$F_3C-COOH$.

The cyclic amines of formula III are obtained, for example, by reacting nitroguanidine of formula V

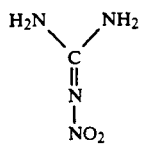
(V)

with a bifunctional amine of the formula

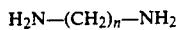
$H_2N-(CH_2)_n-NH_2$ or by reacting nitro-bismercaptoethylene of formula VI

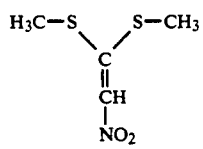
(VI)

with a bifunctional amine of the above formula.

It has now been found that the compounds of formula I according to the invention are valuable active ingredients in pest control while being well tolerated by warm-blooded animals, fish, birds and plants. The compounds according to the invention can be used especially against insects that cause damage to useful plants and ornamentals in agriculture, especially in cotton, vegetable and fruit crops, and in forestry, and can be used in the protection of stored goods and material stocks, and also in the hygiene sector, and especially against insects that are harmful to domestic animals and productive livestock. They are effective against all or individual development stages of normally sensitive and also resistant species. Their action may manifest itself in the death of the pests immediately or only at a later date, for example at moulting, or in reduced oviposition and/or a reduced hatching rate. The above-mentioned pests include:

of the order Lepidoptera, for example,

Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortix spp., *Trichoplusia ni* and Yponomeuta spp.;

of the order Coleoptera, for example,

Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

of the order Orthoptera, for example,

Blatta spp., Blattella spp., Gryllotalpa spp., *Leucophaea maderae*, Locusta spp., Periplaneta spp. and Schistocerca spp.;

of the order Isoptera, for example,

Reticulitermes spp.;

of the order Psocoptera, for example,

Liposcelis spp.;

of the order Anoplura, for example,

Haematopinus spp., Linognathus spp., Pediculus spp., Pemphigus spp. and Phylloxera spp.;
of the order Mallophaga, for example,
Damalinea spp. and Trichodectes spp.;
of the order Thysanoptera, for example,
Frankliniella spp., Hercinothrips spp., Taeniothrips spp., *Thrips palmi, Thrips tabaci* and *Scirtothrips aurantii;*
of the order Heteroptera, for example,
Cimex spp., *Distantiella theobroma*, Dysdercus spp., Euchistus spp., Eurygaster spp., Leptocorisa spp., Nezara spp., Piesma spp., Rhodnius spp., *Sahlbergella singularis*, Scotinophara spp. and Triatoma spp.;
of the order Homoptera, for example,
*Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma larigerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;*
of the order Hymenoptera, for example,
Acromyrmex, Atta spp., Cephus spp., Diprion spp., Diprionidae, *Gilpinia polytoma*, Hoplocampa spp., Lasius spp., *Monomorium pharaonis*, Neodiprion spp., Solenopsis spp. and Vespa spp.;
of the order Diptera, for example,
Aedes spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp. *Oscinella frit, Pegomyia hyoscyami*, Phorbia spp., *Rhagoletis pomonella*, Sciara spp., Stomoxys spp., Tabanus spp., Tannia spp. and Tipula spp.;
of the order Siphonaptera, for example,
Ceratophyllus spp., *Xenopsylla cheopis*; and
of the order Thysanura, for example,
*Lepisma saccharina*.

A particular advantage of the compounds of formula I according to the invention has proved to be that, when the crop plants are treated, the beneficial organisms living on them are largely protected. These beneficial organisms are generally insects and arachnids of the order Acarina which are useful or even necessary in the cultivation of crop plants in that they destroy pests of crop plants or are indispensable, for example, for pollination of the crop plants. In this connection, special mention is to be made of predator mites of the family Cheyletidae and the associated genus Amblyseius, such as the species *Amblyseius fallacis*; ichneumon flies of the family Ichneumonidae; ladybirds of the family Coccinellidae; spiders of the family Lycosidae and the associated genus Lycosa; spiders of the family Oxypidae and the associated genus Oxyopes; bees, especially honeybees, and finally, in the interests of natural hygiene, also ants.

A further advantage of the compounds of formula I according to the invention is their advantageous environmental behaviour. It has been found that undesired residues of compounds of formula I are readily broken down in the soil. In particular, it has been found that the decomposition times of the compounds according to the invention are markedly shorter than corresponding values for the nitroguanidines and nitroethylenes of EP-A-192 060 known from the prior art.

The compounds of formula I are suitable especially for controlling pests in vegetable, rice and sugar-beet crops, such as aphids and rice cicadas.

The good pesticidal activity of the compounds of formula I according to the invention corresponds to a mortality of at least 50-60% of the mentioned pests.

The activity of the compounds of the invention and of the compositions comprising them can be substantially broadened and adapted to prevailing circumstances by the addition of other insecticides and/or acaricides. Examples of suitable additives include representatives of the following classes of compounds: organophosphorus compounds, nitrophenols and derivatives thereof, formamidines, ureas, carbamates, pyrethroids, chlorinated hydrocarbons, and Bacillus thuringiensis preparations.

The compounds of formula I are used in unmodified form or, preferably, together with the adjuvants conventionally employed in formulation technology, and can therefore be formulated in known manner e.g. into emulsifiable concentrates, directly sprayable or dilutable solutions, dilute emulsions, wettable powders, soluble powders, dusts, granules, and also encapsulations in polymer substances. As with the compositions, the methods of application, such as spraying, atomising, dusting, scattering or pouring, are chosen in accordance with the intended objectives and the prevailing circumstances. The compounds of formula I are also suitable for use in the treatment of seed. For this purpose it is possible either to treat or dress the seed with the active ingredient or with a formulation comprising the active ingredient before sowing, or to apply the active ingredient into the seed furrow at the time of sowing.

The formulations, i.e. the compositions, preparations or mixtures comprising the compound (active ingredient) of formula I, or combinations of those compounds with other insecticides or acaricides, and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the $C_8$ to $C_{12}$ fractions of alkylbenzenes, e.g. xylene mixtures or alkylated naphthalenes, aliphatic or cycloaliphatic hydrocarbons such as cyclohexane, paraffins or tetrahydronaphthalene, alcohols such as ethanol, propanol or butanol, and glycols and their ethers and esters, such as propylene glycol, dipropylene glycol ether, ethylene glycol, ethylene glycol monomethyl or monoethyl ether, ketones such as cyclohexanone, isophorone or diacetone alcohol, strongly polar solvents such as N-methyl-2-pyrrolidone, dimethyl sulfoxide or dimethylformamide, or water, vegetable oils such as rape oil, castor oil, coconut oil or soybean oil; and, where appropriate, silicone oils.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of granulated materials of inorganic or organic nature can be used, e.g. especially dolomite or pulverised plant residues.

Depending on the nature of the compound of formula I to be formulated, or of the combinations of those compounds with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 and 18 carbon atoms in the alkyl moiety of the alkylphenols. Further suitable non-ionic surfactants are water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology are described, for example, in the following publications:

"McCutcheon's Detergents and Emulsifiers Annual", MC Publishing Corp., Glen Rock, N.J., USA, 1988", H. Stache, "Tensid-Taschenbuch", 2nd edition, C. Hanser Verlag, Munich, Vienna, 1981, M. and J. Ash, "Encyclopedia of Surfactants", Vol. I–III, Chemical Publishing Co., New York, 1980–1981.

The pesticidal compositions usually comprise 0.1 to 99%, preferably 0.1 to 95%, of a compound of formula I or combinations of that compound with other insecticides or acaricides, 1 to 99.9% of a solid or liquid adjuvant, and 0 to 25%, preferably 0.1 to 25%, of a surfactant. Whereas commercial products will preferably be formulated as concentrates, the end user will normally employ dilute formulations comprising considerably lower active ingredient concentrations. Typical application concentrations are from 0.1 to 1000 ppm, preferably from 0.1 to 500 ppm. The rates of application per hectare are generally from 1 to 1000 g of active ingredient per hectare, preferably from 25 to 500 g/ha.

| Emulsifiable concentrates: | |
|---|---|
| active ingredient: | 1 to 90%, preferably 5 to 20% |
| surface-active agent: | 1 to 30%, preferably 10 to 20% |
| liquid carrier: | 5 to 94%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.5 to 30%, preferably 3 to 15% |
| solid carrier: | 99.5 to 70%, preferably 97 to 85% |

The compositions may also comprise further auxiliaries such as stabilisers, e.g. vegetable oils or epoxidised vegetable oils (epoxidised coconut oil, rape oil or soybean oil), antifoams, e.g. silicon oil, preservatives, viscosity regulators, binders, tackifiers as well as fertilisers or other active ingredients for obtaining special effects.

The following Examples serve to illustrate the invention, but do not limit the invention.

PREPARATION EXAMPLES

Example P1:
2-Chloro-5-(2-nitroimino-imidazolidin-1-ylmethyl)-pyridine-N-oxide

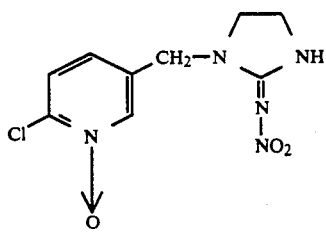

0.85 g of a 55% sodium hydride dispersion in mineral oil is added in portions to a solution of 2.7 g of 2-nitroimino-imidazolidine in 70 ml of acetonitrile. The mixture is stirred for 1.5 hours under a nitrogen atmosphere, and then 3.72 g of 2-chloro-5-chloromethyl-pyridine-N-oxide are added in portions. The reaction mixture is stirred at room temperature for 16 hours and then filtered. The crude product is crystallised out by cooling the filtrate to 0° C. The product is separated off and washed with diethyl ether, yielding pure 2-chloro-5-(2-nitroimino-imidazolidin-1-yl-methyl)-pyridine-N-oxide, m.p. 200° C. (with decomposition).

The compounds of formula I listed in the following Table can be prepared analogously.

TABLE I

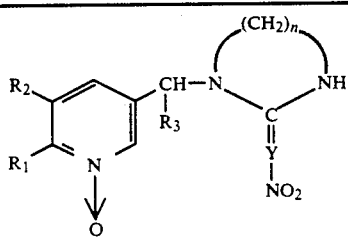

| Comp. No. | $R_1$ | $R_2$ | $R_3$ | Y | n | Phys. data |
|---|---|---|---|---|---|---|
| 1.01 | Cl | H | H | N | 2 | 200° C. (decomp.) |
| 1.02 | Cl | H | H | N | 3 | m.p. 206–208° C. |
| 1.03 | Cl | H | $CH_3$ | N | 2 | |
| 1.04 | Cl | H | $CH_3$ | N | 3 | |
| 1.05 | Cl | H | $C_2H_5$ | N | 2 | |
| 1.06 | Cl | H | H | CH | 2 | 210° C. (decomp.) |
| 1.07 | Cl | H | H | CH | 3 | 220° C. (decomp.) |
| 1.08 | Cl | H | $CH_3$ | CH | 2 | |
| 1.09 | Cl | H | $CH_3$ | CH | 3 | |
| 1.10 | Cl | Cl | H | N | 2 | m.p. 218–220° C. |
| 1.11 | Cl | Cl | H | N | 3 | |
| 1.12 | Cl | Cl | H | CH | 2 | |
| 1.13 | Cl | Cl | H | CH | 3 | m.p. 163–165° C. |
| 1.14 | H | H | H | N | 2 | m.p. 185–188° C. |
| 1.15 | H | H | H | N | 3 | m.p. 193–194° C. |
| 1.16 | H | H | $CH_3$ | N | 2 | |
| 1.17 | H | H | $C_2H_5$ | N | 2 | |
| 1.18 | H | H | $CH_3$ | N | 3 | |
| 1.19 | H | H | H | CH | 2 | 245° C. (decomp.) |
| 1.20 | H | H | H | CH | 3 | 230° C. (decomp.) |
| 1.21 | H | H | $CH_3$ | CH | 2 | |
| 1.22 | H | H | $C_2H_5$ | CH | 2 | |

FORMULATION EXAMPLES

Throughout, Percentages are by Weight)

| Example F1: Emulsifiable concentrates | a) | b) | c) |
|---|---|---|---|
| a compound of Table 1 | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| Example F2: Solutions | a) | b) | c) | d) |
|---|---|---|---|---|
| a compound of Table 1 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160—190° C.) | — | — | 94% | — |

The solutions are suitable for application in the form of micro-drops.

| Example F3: Granules | a) | b) | c) | d) |
|---|---|---|---|---|
| a compound of Table 1 | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in methylene chloride, the solution is sprayed onto the carrier, and the solvent is subsequently evaporated off in vacuo.

| Example F4: Dusts | a) | b) |
|---|---|---|
| a compound of Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| Example F5: Wettable powders | a) | b) | c) |
|---|---|---|---|
| compound no. 1.01 or 1.06 | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62%·1 | 27% | — |

The active ingredient or active ingredient combination is mixed with the adjuvants and the mixture is thoroughly ground in a suitable mill, affording wettable powders which can be diluted with water to give suspensions of any desired concentration.

| Example F6: Emulsifiable concentrate | |
| --- | --- |
| compound no. 1.01 or 1.06 | 10% |
| octylphenol polyethylene glycol ether (4–5 mol of ethylene oxide) | 3% |
| calcium dodecylbenzenesulfonate | 3% |
| castor oil polyglycol ether (36 mol of ethylene oxide) | 4% |
| cyclohexanone | 30% |
| xylene mixture | 50% |

Emulsions of any desired concentration can be obtained from this concentrate by dilution with water.

| Example F7: Dusts | a) | b) |
| --- | --- | --- |
| compound no. 1.19 | 5% | 8% |
| talcum | 95% | — |
| kaolin | — | 92% |

Ready-for-use dusts are obtained by mixing the active ingredient with the carrier and grinding the mixture in a suitable mill.

| Example F8: Extruder granules | |
| --- | --- |
| compound no. 1.19 | 10% |
| sodium lignosulfonate | 2% |
| carboxymethylcellulose | 1% |
| kaolin | 87% |

The active ingredient or active ingredient combination is mixed and ground with the adjuvants, and the mixture is moistened with water. The mixture is extruded, granulated and then dried in a stream of air.

| Example F9: Coated ganules | |
| --- | --- |
| compound no. 1.06 | 3% |
| polyethylene glycol (mol. wt. 200) | 3% |
| kaolin | 94% |

The finely ground active ingredient or active ingredient combination is uniformly applied, in a mixer, to the kaolin moistened with polyethylene glycol. Non-dusty coated granules are obtained in this manner.

| Example F10: Suspension concentrate | |
| --- | --- |
| compound no. 1.01 | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| silicone oil in the form of 75% aqueous emulsion | 1% |
| water | 32% |

The finely ground active ingredient or active ingredient combination is intimately mixed with the adjuvants, giving a suspension concentrate from which suspensions of any desired concentration can be obtained by dilution with water.

BIOLOGICAL EXAMPLES

Example B1: Action against *Nilaparvata lugens*

Rice plants are sprayed with an aqueous emulsion comprising 400 ppm of test compound. After the spray coating has dried, the rice plants are populated with cicada larvae in the 2nd and 3rd stages. Evaluation is made 21 days later. The percentage reduction in the population (% activity) is determined by comparing the number of surviving cicadas on the treated plants with that on untreated plants.

Compounds of Table 1 exhibit good activity against *Nilaparvata lugens* in this test. In particular, compounds 1.01, 1.06, 1.07, 1.14, 1.15, 1.19 and 1.20 are more than 80% effective.

Example B2: Action against *Nephotettix cincticeps*

Rice plants are sprayed with an aqueous emulsion comprising 400 ppm of test compound. After the spray coating has dried, the rice plants are populated with cicada larvae in the 2nd and 3rd stages. Evaluation is made 21 days later. The percentage reduction in the population (% activity) is determined by comparing the number of surviving cicadas on the treated plants with that on untreated plants.

Compounds of Table 1 exhibit good activity against *Nephotettix cincticeps* in this test. In particular, compounds 1.01, 1.06, 1.07, 1.15, 1.19 and 1.20 are more than 80% effective.

Example B3: Action against *Diabrotica balteata* Larvae

Maize seedlings are sprayed with an aqueous emulsion comprising 400 ppm of test compound. After the spray coating has dried, the maize seedlings are populated with 10 *Diabrotica balteata* larvae in the 2nd stage and placed in a plastics container. Evaluation is made 6 days later. The percentage reduction in the population (% activity) is determined by comparing the number of dead larvae on the treated plants with that on untreated plants.

Compounds of Table 1 exhibit good activity against *Diabrotica balteata* in this test. In particular, compounds 1.01, 1.02, 1.06 and 1.20 are more than 80% effective.

Example B4: Action against *Heliothis virescens* Caterpillars

Young soybean plants are sprayed with an aqueous emulsion comprising 400 ppm of the test compound. After the spray coating has dried, the soybean plants are populated with 10 *Heliothis virescens* caterpillars in the first stage and placed in a plastics container. Evaluation is made 6 days later. The percentage reduction in the population and the percentage reduction in feeding damage (% activity) is determined by comparing the number of dead caterpillars and the feeding damage on the treated plants with that on untreated plants.

Compounds of Table 1 exhibit good activity against *Heliothis virescens* in this test. In particular, compounds 1.01 and 1.06 are more than 80% effective.

Example B5: Action against *Spodoptera littoralis* Caterpillars

Young soybean plants are sprayed with an aqueous emulsion comprising 400 ppm of the test compound. After the spray coating has dried, the soybean plants are populated with 10 *Spodoptera littoralis* caterpillars in the third stage and placed in a plastics container. Evaluation is made 3 days later. The percentage reduction in the population and the percentage reduction in feeding damage (% activity) is determined by comparing the number of dead caterpillars and the feeding damage on the treated plants with that on untreated plants.

Compounds of Table 1 exhibit good activity against *Spodoptera littoralis* in this test. In particular, compounds 1.06 and 1.19 are more than 80% effective.

Example B6: Action against *Aphis craccivora*

Pea seedlings are infested with *Aphis craccivora* and then sprayed with a spray mixture comprising 400 ppm of the test compound, and incubated at 20° C. Evaluation is made 3 and 6 days later. The percentage reduction in the population (% activity) is determined by comparing the number of dead aphids on the treated plants with that on untreated plants.

Compounds of Table 1 exhibit good activity against *Aphis craccivora* in this test. In particular, compounds 1.01, 1.02, 1.06, 1.07, 1.15, 1.19 and 1.20 are more than 80% effective.

Example B7: Systemic Action against *Nilaparvata lugens*

Pots containing rice plants are placed in an aqueous emulsion solution comprising 400 ppm of the test compound. The rice plants are then populated with larvae in the 2nd and 3rd stages. Evaluation is made 6 days later. The percentage reduction in the population (% activity) is determined by comparing the number of cicadas on the treated plants with that on untreated plants.

Compounds of Table 1 exhibit good activity against *Nilaparvata lugens* in this test. In particular, compounds 1.01, 1.02, 1.06, 1.07, 1.10, 1.14, 1.15, 1.19 and 1.20 are more than 80% effective.

Example B8: Systemic Action against *Nephotettix cincticeps*

Pots containing rice plants are placed in an aqueous emulsion solution comprising 400 ppm of the test compound. The rice plants are then populated with larvae in the 2nd and 3rd stages. Evaluation is made 6 days later. The percentage reduction in the population (% activity) is determined by comparing the number of cicadas on the treated plants with that on untreated plants.

Compounds of Table 1 exhibit good activity against *Nephotettix cincticeps* in this test. In particular, compounds 1.01, 1.06, 1.07, 1.15, 1.19 and 1.20 are more than 80% effective.

Example B9: Systemic Action against *Myzus persicae*

Pea seedlings are infested with *Myzus persicae* and then placed with their roots in a spray mixture comprising 400 ppm of the test compound, and incubated at 20° C. Evaluation is made 3 and 6 days later. The percentage reduction in the population (% activity) is determined by comparing the number of dead aphids on the treated plants with that on untreated plants.

Compounds of Table 1 exhibit good activity against *Myzus persicae* in this test. In particular, compounds 1.01, 1.06, 1.07, 1.19 and 1.20 are more than 80% effective.

Example B10: Action against *Anthonomus grandis* Adults

Young cotton plants are sprayed with an aqueous emulsion comprising 400 ppm of the test compound. After the spray coating has dried, the cotton plants are populated with 10 adults of *Anthonomus grandis* and placed in a plastics container. Evaluation is made 3 days later. The percentage reduction in the population and the percentage reduction in feeding damage (% activity) is determined by comparing the number of dead beetles and the feeding damage on the treated plants with that on untreated plants.

Compounds of Table 1 exhibit good activity against *Anthonomus grandis* in this test. In particular, compound 1.06 is more than 80% effective.

Example B11: Action against *Bemisia tabaci*

Dwarf bean plants are placed in gauze cages and populated with adults of *Bemisia tabaci* (whitefly). When oviposition has taken place, all the adults are removed and 10 days later the plants and the nymphs located thereon are sprayed with an aqueous emulsion of the test compounds (concentration 400 ppm). Evaluation is made 14 days after application of the test compound by determining the % hatching rate in comparison with untreated controls.

Compounds of Table 1 exhibit good activity against *Bemisia tabaci* in this test. In particular, compound 1.06 is more than 80% effective.

Example B12: Action against *Myzus persicae*

Pea seedlings are infested with *Myzus persicae* and then sprayed with a spray mixture comprising 400 ppm of the test compound, and incubated at 20° C. Evaluation is made 3 and 6 days later. The percentage reduction in the population (% activity) is determined by comparing the number of dead aphids on the treated plants with that on untreated plants.

Compounds of Table 1 exhibit good activity against *Myzus persicae* in this test. In particular, compounds 1.01, 1.06 and 1.19 are more than 80% effective.

Example B13: Action against *Amblyseius fallacis* (Predator Mite)

Young bean plants are sprayed with an aqueous emulsion comprising 50 ppm of the test compound. 0, 2 and 4 days after the treatment, 40 females of *Amblyseius fallacis* are placed on the leaves and fed with spider mites of the species *Tetranychus urticae*. Evaluation is made 4 days after the predator mites were placed on the plants. The percentage reduction in the population (% activity) is determined by comparing the number of dead eggs, larvae and adults on the treated plants with that on untreated plants.

Compounds of Table 1 are no more than 20% effective in this test. In particular, compound 1.01, even at a concentration of 400 ppm, does not exhibit a mortality effect greater than 20% against *Amblyseius fallacis* in any of the three test series, while the compound 2-chloro-5-(2-nitroimino-imidazolidin-1-ylmethyl)pyridine known from the prior art causes more than 50% damage to the predator mite population at concentration of only 50 ppm.

Example B14: Action against *Lucilia cuprina* Blowflies

Fresh egg deposits of the blowfly species *Lucilia cuprina* are placed in small portions (30–50 eggs) in test tubes in which 4 ml of nutrient medium have previously been mixed with 1 ml of test solution comprising 16 ppm of the test compound. After inoculation of the culture medium, the test tubes are closed with a cotton wool plug and incubated in an incubator for 4 days at 30° C. Larvae about 1 cm long (stage 3) have developed in the untreated medium by the end of this period. If the test compound is active, the larvae are either dead or markedly retarded at the end of that period. Evaluation is made after 96 hours.

Compounds of Table 1 exhibit good activity against Lucilia cuprina in this test. In particular, compounds 1.01, 1.06 and 1.07 are more than 80% effective.

Example B15: Action against *Ctenocephalides felis*

20 to 25 flea eggs are placed in a horizontal 50 ml cell culture bottle into which 15 g of flea larvae nutrient medium comprising 100 ppm of the test compound have been introduced beforehand. The test bottles are incubated in an incubator at 26°–27° C. and 60–70% humidity. After 21 days, the bottles are checked for the presence of adult fleas, unhatched pupae and larvae.

Compounds of Table 1 exhibit good activity against *Ctenocephalides felis* in this test.

What is claimed is:

1. The compound 2-chloro5-(2-nitroimino-imidazolidin-1-ylmethyl)-pyridine-N-oxide.

2. An insecticidal composition comprising the compound 2-chloro5-(2-nitroimino-imidazolidin-1-ylmethyl)-pyridine-N-oxide as active ingredient, and a carrier.

3. A method of controlling insects that are harmful to animals and plants, which comprises applying an insecticidally effective amount of the compound of claim 1 to the insects.

* * * * *